US010655097B2

(12) United States Patent
Johnson et al.

(10) Patent No.: US 10,655,097 B2
(45) Date of Patent: May 19, 2020

(54) T-CELL CULTURE DOUBLE BAG ASSEMBLY

(71) Applicant: Saint-Gobain Performance Plastics Corporation, Aurora, OH (US)

(72) Inventors: Scott Richard Johnson, Troy, NY (US); Daniel Salvatore Montuori, Niskayuna, NY (US)

(73) Assignee: Saint-Gobain Performance Plastics Corporation, Solon, OH (US)

(*) Notice: Subject to any disclaimer, the term of this patent is extended or adjusted under 35 U.S.C. 154(b) by 0 days.

(21) Appl. No.: 14/976,027

(22) Filed: Dec. 21, 2015

(65) Prior Publication Data

US 2016/0177245 A1 Jun. 23, 2016

Related U.S. Application Data

(60) Provisional application No. 62/095,124, filed on Dec. 22, 2014.

(51) Int. Cl.
*C12M 1/00* (2006.01)
*C12M 1/04* (2006.01)

(52) U.S. Cl.
CPC ............ *C12M 23/14* (2013.01); *C12M 23/20* (2013.01); *C12M 23/24* (2013.01); *C12M 29/04* (2013.01)

(58) Field of Classification Search
CPC ...... C12M 23/14; C12M 23/20; C12M 23/24; C12M 29/04
See application file for complete search history.

(56) References Cited

U.S. PATENT DOCUMENTS

| | | | |
|---|---|---|---|
| 3,030,290 A | 4/1962 | Ryan et al. |
| 3,255,099 A | 6/1966 | Wolinski |
| 3,274,089 A | 9/1966 | Wolinski |
| 3,274,090 A | 9/1966 | Amborski |
| 3,274,091 A | 9/1966 | Amborski |

(Continued)

FOREIGN PATENT DOCUMENTS

| EP | 0725134 A2 | 8/1996 |
|---|---|---|
| WO | WO 2012031234 A2 | 3/2012 |

(Continued)

OTHER PUBLICATIONS

International Search Report and Written Opinion, PCT/US2015/067274, dated May 16, 2016, 16 pages.

(Continued)

*Primary Examiner* — Michael L Hobbs
(74) *Attorney, Agent, or Firm* — McDonnell Boehnen Hulbert & Berghoff LLP (57) ABSTRACT

A cell culture bag is provided, comprising a framed porous inner fluoropolymer bag that allows for growing and harvesting cells and an outer fluoropolymer bag that allows removal and replenishing feed media without loss of cells. In one embodiment, a bag comprising an outer bag and an inner bag is presented. The outer bag comprises a gas permeable porous film having a first port and a second port attached thereto and the inner bag comprises a gas permeable porous film having a third port attached thereto that passes through the outer bag to the inner bag. The inner bag has larger pore size than the outer bag to allow movement of media between the outer bag and the inner bag.

22 Claims, 4 Drawing Sheets

(56) References Cited

U.S. PATENT DOCUMENTS

| | | | |
|---|---|---|---|
| 3,275,540 | A | 9/1966 | McBride |
| 3,284,331 | A | 11/1966 | McBride et al. |
| 3,291,712 | A | 12/1966 | McBride |
| 3,296,011 | A | 1/1967 | McBride et al. |
| 3,391,314 | A | 7/1968 | Carter |
| 3,397,132 | A | 8/1968 | Wolinski |
| 3,485,734 | A | 12/1969 | Pecka |
| 3,507,763 | A | 4/1970 | McBride |
| 3,676,181 | A | 7/1972 | Kowalewski |
| 4,549,921 | A | 10/1985 | Wolfe |
| 4,661,455 | A | 4/1987 | Hubbard |
| 4,829,002 | A | 5/1989 | Pattillo et al. |
| 4,847,462 | A | 7/1989 | Soodak et al. |
| 4,937,194 | A | 6/1990 | Pattillo et al. |
| 4,945,203 | A | 7/1990 | Soodak et al. |
| 5,057,429 | A * | 10/1991 | Watanabe ............ B01F 9/0001 206/213.1 |
| 5,071,760 | A | 12/1991 | Watanabe et al. |
| 5,225,346 | A | 7/1993 | Matsumiya et al. |
| 5,686,304 | A | 11/1997 | Codner |
| 5,935,847 | A * | 8/1999 | Smith ................... C12M 23/14 383/102 |
| 6,060,317 | A | 5/2000 | Malech |
| 6,297,046 | B1 | 10/2001 | Smith et al. |
| 6,638,728 | B1 | 10/2003 | Desai et al. |
| 6,726,979 | B2 | 4/2004 | Friedman et al. |
| 7,316,932 | B2 | 1/2008 | Woodside |
| 7,329,742 | B2 | 2/2008 | Doyle et al. |
| 7,514,075 | B2 | 4/2009 | Hedrick et al. |
| 7,560,274 | B1 * | 7/2009 | Fuller ................... C12M 23/24 383/102 |
| 8,138,289 | B2 | 3/2012 | Kofinas et al. |
| 8,318,438 | B2 | 11/2012 | Vivekananda et al. |
| 8,512,566 | B2 | 8/2013 | Griffin et al. |
| 8,727,132 | B2 | 5/2014 | Miltenyi et al. |
| 8,747,289 | B2 | 6/2014 | Coelho |
| 2003/0162190 | A1 | 8/2003 | Gorenstein et al. |
| 2005/0221486 | A1 | 10/2005 | Lin et al. |
| 2006/0246546 | A1 | 11/2006 | Jenkins et al. |
| 2008/0118974 | A1 | 5/2008 | Martin et al. |
| 2009/0239762 | A1 | 9/2009 | Tan et al. |
| 2009/0298164 | A1 * | 12/2009 | Cattadoris .......... B29C 45/0053 435/294.1 |
| 2009/0305389 | A1 | 12/2009 | Willson et al. |
| 2010/0248361 | A1 | 9/2010 | Lasky et al. |
| 2012/0142088 | A1 | 7/2012 | Hsiao et al. |
| 2012/0238011 | A1 | 9/2012 | Tuohey et al. |
| 2013/0011896 | A1 | 1/2013 | Strehler |
| 2013/0040837 | A1 | 2/2013 | Karp et al. |
| 2013/0109086 | A1 | 5/2013 | Kobayashi et al. |
| 2013/0130361 | A1 | 5/2013 | Okano et al. |
| 2013/0236335 | A1 | 9/2013 | Nelson et al. |
| 2014/0066281 | A1 | 3/2014 | Weasler et al. |
| 2014/0227769 | A1 * | 8/2014 | Strobbe .................. C12M 23/34 435/287.1 |
| 2014/0287512 | A1 | 9/2014 | Kaisermayer et al. |

FOREIGN PATENT DOCUMENTS

| | | |
|---|---|---|
| WO | WO 2012076190 A1 | 6/2012 |
| WO | WO 2013049860 A1 | 4/2013 |
| WO | WO 2014120344 A2 | 8/2014 |

OTHER PUBLICATIONS

Albers, et al., "Structural and Functional Characteristics of Chimeric Avidins Physically Adsorbed onto Functionalized Polythiophene Thin Films." *ACS Applied Materials & Interfaces*, 2012, pp. 4067-4077.

Antharavally, et al., "Quantitation of Proteins using a Dye-metal-based Colorimetric Protein Assay." Analytical Biochemistry, No. 385, 2009, pp. 342-345.

Balamurugan, et al. "Surface immobilization methods for aptamer diagnostic applications" *Anal Bioanal Chem*, No. 390, 2008, pp. 1009-1021.

Coates, "Interpretation of Infrared Spectra, A Practical Approach." In Encyclopedia of Analytical Chemistry, Chichester: John Wiley & Sons, 2000, pp. 10815-10837.

Drumheller, et al., "Surface Immobilization of Adhesion Ligands for Investigation of Cell-Substreate Interactions", CRC Press LLC, 2003, pp. 9.1-9.14.

Fabre, et al., "Immobilization of Double Functionalized Carbon Nanotubes on Glassy Carbon Electrodes for the Electrochemical Sensing of the Biotin-avidin Affinity." *Journal of Electroanalytical Chemistry*, No. 665, 2012, pp. 90-94.

Gauvreau, et al. "Engineering Surfaces for Bioconjugation: Developing Strategies and Quantifying the Extent of the Reactions." *Bioconjugate Chem.*, 2004, pp. 1146-1156.

Heikkinen, et al., "Covalent Biofunctionalization of Cellulose Acetate with Thermostable Chimeric Avidin." *ACS Appl. Mater. Interfaces*, No. 3, 2011, pp. 2240-2245.

Lachmann, et al., "Surface modification of closed plastic bags for adherent cell cultivation." *Eur. Phys. J. Appl. Phys.*, No. 55, 2011, p. 13812.

McGettrick, et al., "A Substrate-Independent Approach for the Surface Immobilization of Oligonucleotides using Aldehyde Functionalized Surfaces." *Chem. Vap. Deposition*, No. 15, 2009, pp. 122-127.

Ocana, et al., "A Comparison of four protocols for the immobilization of an aptamer on graphite composite electrodes." Microchim Acta, No. 181, 2014, pp. 355-363.

Oh, et al., "Surface Modification for DNA and Protein Microarrays." *Journal of Integrative Biology*, vol. 10, No. 3, 2006, pp. 327-343.

Orelma, et al., "Generic Method for Attaching Biomolecules via Avidin-Biotin Complexes Immobilized on Films of Regenerated and Nanofibrillar Cellulose." *Biomacromolecules*, No. 13, 2012, pp. 2802-2810.

Ozer, et al., "New Technologies Provide Quantum Changes in the Scale, Speed, and Success of SELEX Methods nd Aptamer Characterization" *Molecular Therapy—Nucleic Acids*, No. 3, e183, 2014 pp. 1-18.

Ponche, et al., "Protein/Material Interfaces: Investigation on Model Surfaces." Journal of Adhesion Science and Technology, No. 24, 2010, pp. 2141-2164.

Rabe, et al,. "Understanding Protein Adsorption Phenomena at Solid Surfaces." *Advances in Colloid and Interface Science*, No. 162, 2011, pp. 87-106.

Racine, et al., "A Versatile Gradient of Biomolecules for Regulating Cell Behaviour." Journal of Adhesion Science and Technology, No. 24, 2010, pp. 975-992.

Srivastava, et al. "Polymer-antibody fragment conjugates for biomedical applications." *Progress in Polymer Science*, 2014, pp. 308-329.

Sromqvist, et al., "Binding of biotin to Streptavidin: A combined fluorescence correlation spectroscopy and time-resolved fluorescence study." The European Physical Journal, 2011, pp. 181-194.

Sun, et al., "Oligonucleotide Aptamers: New Tools for Targeted Cancer Therapy" *Molecular Therapy—Nucleic Acids*, 2014, pp. 1-14.

Tadahiro Ohmi, Ultra-Clean Technology Handbook: vol. 1: Ultra-Pure Water, CRC Press, 1993, pp. 497-517.

Tong, et al., "Peptide surface modification of poly(tetrafluoroethylene-co-hexafluoropropylene) enhances its interaction with central nervous system neurons." *Journal of Biomedical Materials Research*, 1998, pp. 85-95.

Vermette, et al., "Immobilization and Surface Characterization of Neutravidin Biotin-binding Protein on Different Hydrogel Interlayers." *Journal of Colloid and Interface Science*, No. 259, 2003, pp. 13-26.

Vesel, et al., "Adsorption of Protein Streptavidin to the Plasma Treated Surface of Polystyrene." *Applied Surface Science* 258, 2012, pp. 5558-5560.

Vesel, et al., "Immobilization of Protein Streptavidin to the Surface of PMMA Polymer." *Vacuum*, No. 86, 2012, pp. 773-775.

(56) References Cited

OTHER PUBLICATIONS

Xia, et al., "Ultra Sensitive Affinity Chromatography on Avidin-functionalized PMMA Microchip for Low Abundant Post-translational Modified Protein Enrichment." *Biomedical Microdevices*, 2012 pp. 67-81.

Ye, et al., "Generating Aptamers by Cell-SELEX for Applications in Molecular Medicine" *Int. J. Mot Sci.*, No. 13, 2012, pp. 3341-3353.

Yun, et al., "Human monocyte/macrophage adhesion and cytokine production on surface-modified poly(tetrafluoroethylene/hexafluoropropylene) polymers with and without protein preadsorption." *Journal of Biomedical Materials Research*, vol. 29, 1995, pp. 257-268.

Zhou, et al., "Cell-type-specific, Aptamer-functionalized Agents for Targeted Disease Therapy" *Molecular Therapy—Nucleic Acids*, 2014, pp. 1-17.

\* cited by examiner

T-CELL CULTURE DOUBLE BAG ASSEMBLY

CROSS REFERENCE TO RELATED APPLICATIONS

This application claims benefit under 35 U.S.C. § 119(e) to U.S. Ser. No. 62/095,124, entitled "T-CELL CULTURE DOUBLE BAG ASSEMBLY", filed Dec. 22, 2014, the contents of which is incorporated herein by reference in their entirety.

FIELD OF THE INVENTION

The invention relates generally to a cell culture apparatus and a cell culture method

BACKGROUND OF THE INVENTION

Cell culture is the complex process by which cells are grown under controlled conditions, generally outside of their natural environment. In practice cell culture refers to the culturing of cells derived from multi-cellular eukaryotes, especially animal cells. However, there are also cultures of plants, fungi, insects and microbes, including viruses, bacteria and protista.

Cells are grown and maintained at an appropriate temperature and gas mixture (typically, 37° C., 5% $CO_2$ for mammalian cells) in a cell incubator. Culture conditions vary widely for each cell type, and variation of conditions for a particular cell type can result in different phenotypes.

A variety of cell types are grown in vitro and similarly a variety of media are available depending on the particular growth requirements of the cells and the growth conditions.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. They are called T cells because they mature in the thymus. There are several subsets of T cells, each with a distinct function, including T helper cells, cytotoxic T cells, memory T cells, regulatory T cells, natural killer T cells, and mucosal associated invariant T cells.

Many devices have been developed for culturing cells, which can be divided into three categories: 1) small-scale devices with a culture volume typically between 1 L to 20 L, although culture volumes of less than 1 L, even in the range of 10 mL or 100 mL are not exceptional; 2) medium-scale devices with culture volumes between 20 and 2,000 L; and 3) large-scale bioreactors with operating volumes from 2,000 up to 20,000 L. In general, small-scale devices are limited to a few liters in volume because they rely on surface oxygen transfer to provide aeration for cells. Examples of small-scale devices include multiple well tissue culture plates, spinner flasks, T-flasks, roller bottles, and cell culture bags.

Commercially available gas permeable cell culture devices in the form of bags are currently a standard device format used for cell culture. Cell culture bags have the advantage of being disposable, which reduces preparation and clean up time. Additionally, cell culture bags are pre-sterilizable, inexpensive, easy to use and require minimal space for storage and use.

Gas permeable fluoropolymer cell culture bags are commercially available from OriGen Biomedical Group (OriGen PermaLife™ Bags), Baxter (Lifecell® X-Fold™ related to U.S. Pat. Nos. 4,829,002, 4,937,194, 5,935,847, 6,297,046 B1), Medtronic (Si-Culture™, U.S. Pat. No. 5,686,304), Biovectra (VectraCell™), and American Fluoroseal (VueLife™ Culture Bag System, covered by U.S. Pat. Nos. 4,847,462 and 4,945,203).

One problem of conventional fluoropolymer cell culture bags is that the feed media and cells are mixed within the culture chamber and therefore the amount of media added is limited to the volume of the container. In one example, Matsumiya et al. (U.S. Pat. No. 5,225,346) attempts to correct the problem of media supply by integrating the bag with a medium storage compartment. The culture chamber and medium storage compartment are connected and when fresh medium is needed it is passed from the medium storage compartment to the culture chamber.

Another problem of conventional fluoropolymer cell culture bags is removal of media having diminished nutrient content and increased waste content during cell cultivation which unavailingly removes the desired cells as well.

Therefore, a need exists for the removal and replenishment of feed media without diminishing cell count thereby advantageously concentrating cells over a period of time not controlled by feed media supply limitations.

BRIEF SUMMARY OF THE INVENTION

An apparatus and method for cell cultivation that overcomes one or more of the disadvantages known in the art is provided. It has been discovered that it is possible to prepare a cell culture bag comprising a framed porous inner gas permeable bag that allows for growing and harvesting cells contained within an outer gas permeable bag that allows removal and replenishing feed media without loss of cells.

In one embodiment, a bag comprising an outer bag and an inner bag is presented. The outer bag comprises a gas permeable porous film having a first port and a second port attached thereto and the inner bag comprises a gas permeable porous film having a third port attached thereto that passes through the outer bag to the inner bag. The inner bag has larger pore size than the outer bag to allow movement of media between the outer bag and the inner bag.

In another embodiment the gas permeable film of the outer bag comprises FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifluoroethylene-vinylidene fluoride copolymer), TFE/HFP (tetrafuoroethylene-hexafuoropropylene copolymer), or mixtures thereof.

In another embodiment the first and second ports of the outer bag comprise tubes attached to the outer bag.

In another embodiment the third port of the inner bag comprises a tube attached to the inner bag.

In another embodiment the tubes attached to the inner and outer bags comprises FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), TFE/HFP (tetrafuoroethylene-hexafuoropropylene copolymer), or mixtures thereof.

In another embodiment the nonbonded ends of the tubes attached to the inner or outer bags contain needle openings.

In another embodiment the tubes are attached to the inner or outer bags by chemical bonding, adhesive bonding, thermal fusion bonding, solvent bonding, laser welding, surface treatment, or combinations thereof.

In another embodiment the gas permeable film of the inner bag comprises FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), TFE/HFP (tetrafuoroethylene-hexafuoropropylene copolymer), or mixtures thereof.

In one aspect the pore size of the gas permeable film of the inner bag is between about 1 microns to about 6 microns in diameter.

In another aspect the pore size of the gas permeable film of the inner bag is between about 1.5 microns to about 5 microns in diameter.

In another aspect the pore size of the gas permeable film of the inner bag is between about 2 microns to about 4 microns in diameter.

In another aspect the pore size of the gas permeable film of the inner bag is between about 2.5 microns to about 3.5 microns in diameter.

In still another aspect the pore size of the gas permeable film of the inner bag is about 3 microns in diameter.

In another aspect the porosity of the gas permeable film of the inner bag is at least 20%.

In another aspect the porosity of the gas permeable film of the inner bag is at least 30%.

In still another aspect the porosity of the gas permeable film of the inner bag is about 50%.

In another embodiment the inner bag is secured by a fluoropolymer frame and beading.

In still another embodiment the fluoropolymer frame and beading are PTFE, FEP, PFA, or an inert fluoropolymer.

In another embodiment a method is disclosed to cultivate cells in a bag comprising adding cells and media to an oxygen permeable bag. The bag comprises an outer bag and an inner bag. The outer bag comprises a gas permeable film having a first port and a second port attached thereto. The inner bag comprises a gas permeable film having a third port attached thereto that passes through the outer bag to the inner bag. The gas permeable film of the inner bag has increased pore size compared to the outer bag to allow movement of media between the outer bag and the inner bag.

In one aspect the cells comprise connective tissue cells, skeletal cells, cardiac cells, epithelial cells, neural cells, endocrine cells, immune cells, lymphocytes, melanocytes, tumor cells, or mixtures thereof.

In another aspect the media is added to the bag wherein the media is contained within the outer bag and the inner bag.

In still another aspect the bag is incubated.

In another embodiment the diameter of the pores is sufficiently small enough to retain the cells within the inner bag.

In another embodiment the media can be added through the first port and removed through the second port.

In another embodiment the cells can be introduced or removed through the third port.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The current disclosure allows for the removal and replenishment of feed media from a cell culture apparatus without diminishing cell count thereby advantageously concentrating cells over a period of time not controlled by feed media supply limitations.

The culture bag disclosed comprises a gas permeable outer bag with at least four ports that allow access to the interior of the bag. Oxygen is necessary for cellular growth in a medium and carbon dioxide is necessary for a medium to buffer pH. A pH range of 7.4-7.6 is optimal for normal cell growth and pH that fall outside of this range, for example, a pH higher than 7.8 can inhibit normal cell growth. Therefore it is necessary for the culture bag to have good gas permeability to oxygen and carbon dioxide.

Those skilled in the art will recognize that the gas permeable material should be selected based on a variety of characteristics including flexibility, heat-sealability that ensures airtightness, good clarity that permits the microscopic examination of cell growth, freedom from plasticizers (such as dioctyl phthalate and diisodecyl phthalate) which are toxic to cells, moisture vapor transmission, capacity to be altered for desired cell interaction with cells, optical clarity, physical strength, and the like. The current embodiments described herein are devoid of such materials.

Gas permeable fluoropolymers are a preferred choice for culture bags because they are biologically, chemically and immunologically inert. The film of the outer bag of the current invention comprises FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or mixtures thereof.

In a preferred embodiment the film of the outer bag is FEP (fluorinated ethylene-propylene).

FEP is a copolymer of hexafluoropropylene and tetrafluoroethylene. It is flexible, extremely resistance to chemical attack, highly transparent, and resistant to sunlight. It is preferred that FEP contains no plasticizers, leachables or extractables that can adversely affect cell cultures. FEP has excellent oxygen, carbon dioxide and nitrogen gas transfer rates and is highly impermeable to water, allowing incubation of cells with minimal water loss. Having high impermeability to water is advantageous as providing additional means for humidification can be a common source for the introduction of mold and fungus contamination.

The thickness of the film of the outer bag can vary upon application and desired container volume. The film thickness of the outer bag may be 0.1 mm to 0.7 mm, 0.2 mm to 0.5 mm, but preferably 0.3 mm. Outer bag volumes may range from 100 mL to 100 L, 500 mL to 20 L, but preferably 1 L to 5 L.

The outer bag comprises two fluoropolymer sheets that are bonded together at their edges to form a sealed compartment. The method of bonding is selected from laser welding, corona discharge, radiation, extreme heat or melt lamination, etching, plasma treatment, wetting, adhesives, or combinations thereof.

In a preferred embodiment the edges of two FEP sheets are laser welded together.

Figure 1:
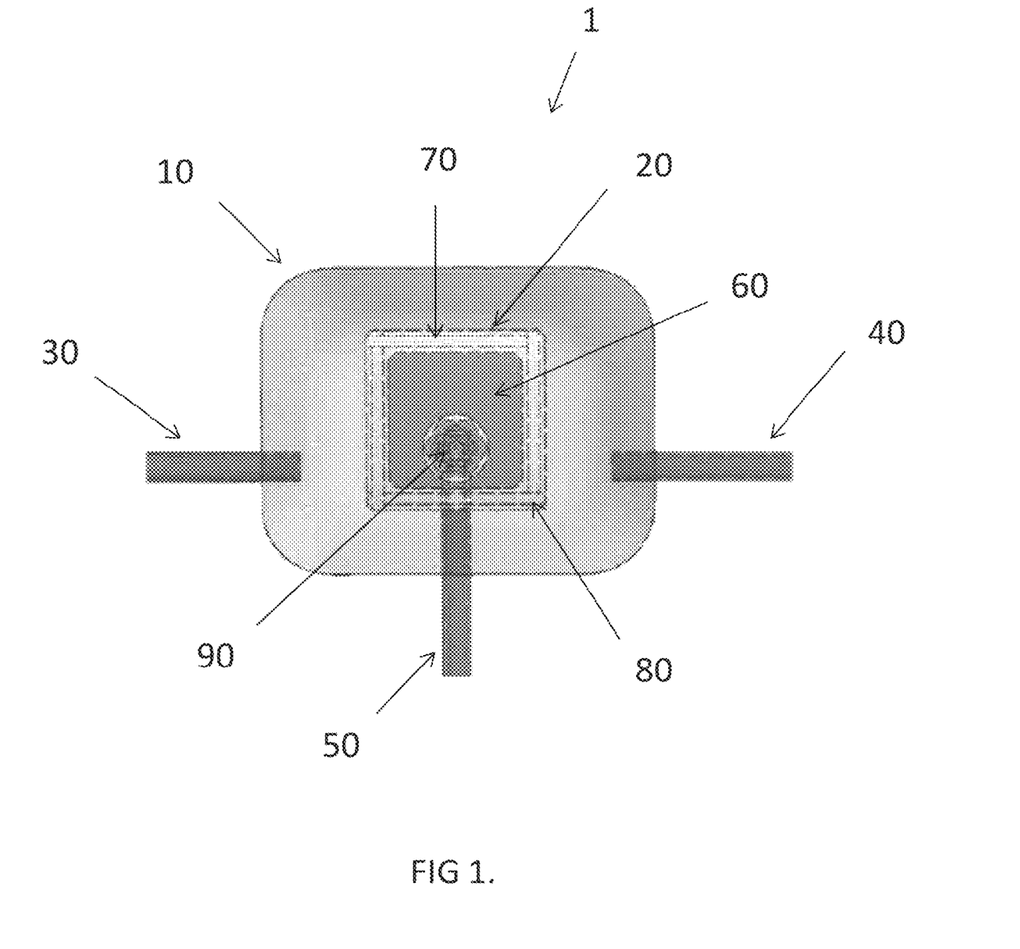
FIG. 1 shows a bottom-plan view of a cell culture apparatus having double bag assembly.

FIG. 1 shows a bottom-plan view of double bag assembly 1. Outer bag 10 has ports 30 and 40 located at opposite ends for feeding and removing waste media from the interior of outer bag 10. A third port 50 is located entering the bottom of outer bag 10 that attaches to inner bag 20. The location of ports 30, 40, and 50 is not restricted to the current configuration and ports 30, 40, and 50 may be positioned for convenience of use or manufacture.

Ports 30, 40, and 50, each individually, comprise fluoropolymer tubes that are bonded in place. The fluoropolymer tubes comprises FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafluoroethylene-hexafuoropropylene copolymer), or mixtures thereof.

The total number of ports is not limited to the current embodiments. A double bag assembly may have at least two ports. One port to provide access to the inner bag and another port to provide access to the outer bag.

In a preferred embodiment the tubes are FEP (fluorinated ethylene-propylene).

The tubes that comprise ports 30, 40, and 50 are bonded to the FEP sheets. The location of ports 30, 40, and 50 is not restricted to the current configuration and ports 30, 40, and 50 may be positioned for convenience of use or manufacture. The method of bonding is selected from laser welding, corona discharge, radiation, extreme heat or melt lamination, etching, plasma treatment, wetting, adhesives, or combinations thereof.

In a preferred embodiment the FEP tubes are bonded to the FEP outer bag by laser welding.

Outer bag 10 is manufactured containing gas permeable inner bag 20. The inner bag comprises the cell cultivation compartment 60 and the film thickness can vary upon application. Inner bag 20 contains pores having pore a diameter of between about 1 microns to about 6 microns in diameter, preferably between about 1.5 microns to about 5 microns in diameter, more preferably between about 2 microns to about 4 microns in diameter, more preferably between about 2.5 microns to about 3.5 microns in diameter, and most preferably about 3 microns in diameter. The pore size within the film allows for movement of media between the inner bag and the outer bag but prevents the cells located within the inner bag from entering the outer bag compartment.

Pore size of the cell cultivation compartment 60 is measure of the pore diameter within a porous material. Pore size in a given material is commonly graded as extra fine, fine, medium, course, and extra course.

Pore size can be selected based on cell type cultivation required. For example an inner film pore size of 1 micron to 3 microns can be selected for T-cells having average diameter of 5 microns.

The film of inner bag 20 of the disclosure comprises FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or mixtures thereof.

In a preferred embodiment the film of the inner bag is PTFE (polytetrafluoroethylene) material, ie. ZITEX®. ZITEX from Saint-Gobain is available in a number of porosities and thicknesses.

Average pore volume or porosity is a measure of the pore density of a material, and is a fraction of the volume of pores over the total volume, usually indicated as a percentage between 0 and 100%. Porosity can be measured by employing several porosimetry methods. These methods include direct, optical, computed tomography, imbibition, water evaporation, mercury intrusion, gas expansion, thermoporosimetry, and cryoporometry methods.

The average pore volume of inner bag 20 in the current embodiments is between about 20% to about 55%, more preferably 30% to about 50%, and most preferably between about 40% to about 45%.

Inner bag 20 comprises two fluoropolymer sheets that are bonded together at their edges to form sealed cell culture compartment 60.

In a preferred embodiment the edges of two PTFE sheets are bonded together by a frame and beading. The round beading is extruded to secure frame 70 to inner bag 20.

Figure 3:
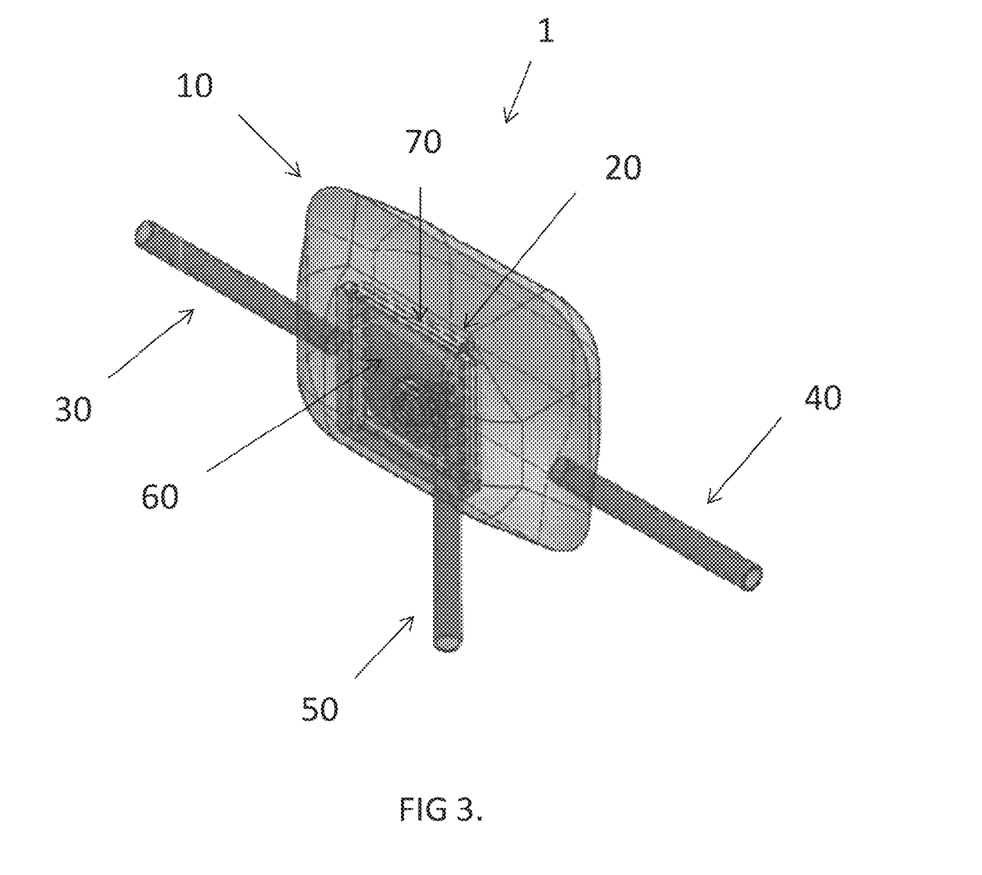
FIG. 3 shows a three-dimensional view of a cell culture apparatus having double bag assembly.

Porous inner bag 20 is supported by fluoropolymer frame 70 and beading 80. The fluoropolymer frame and beading each individually, can comprises FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifluoroethylene-vinylidene fluoride copolymer), and TFE/HFP (tetrafuoroethylene-hexafuoropropylene copolymer), or mixtures thereof.

In a preferred embodiment fluoropolymer frame 70 and beading 80 are each individually PTFE (polytetrafluoroethylene), FEP (fluorinated ethylene-propylene), or PFA (perfluoroalkoxy).

Figure 4:
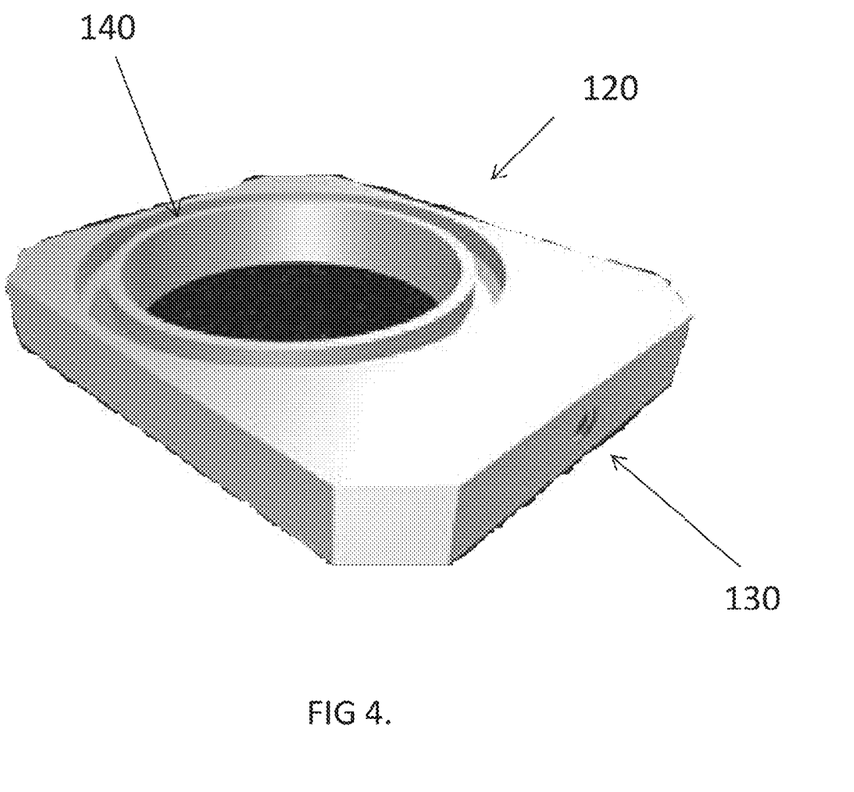
FIG. 4 shows a three-dimensional view of a round frame apparatus.

FIG. 4. depicts another embodiment where square frame 70 can be circular frame 120. Inner bag 20 can be attached to circular frame 120 by beading at ridge 140.

In another embodiment the interior of the inner bag having frame 120 can be accessed through integrated port 130.

Third port 50 comprises fluoropolymer tubing that passes through the outer bag and attaches to the inner bag. The third port that suspends the inner bag, framing and beading comprises a fluoropolymer elbow 90 that attaches the fluoropolymer tubing to the inner bag.

Ports 30, 40, and 50 have sealable openings that allows access to the interior of the bags.

Figure 2:
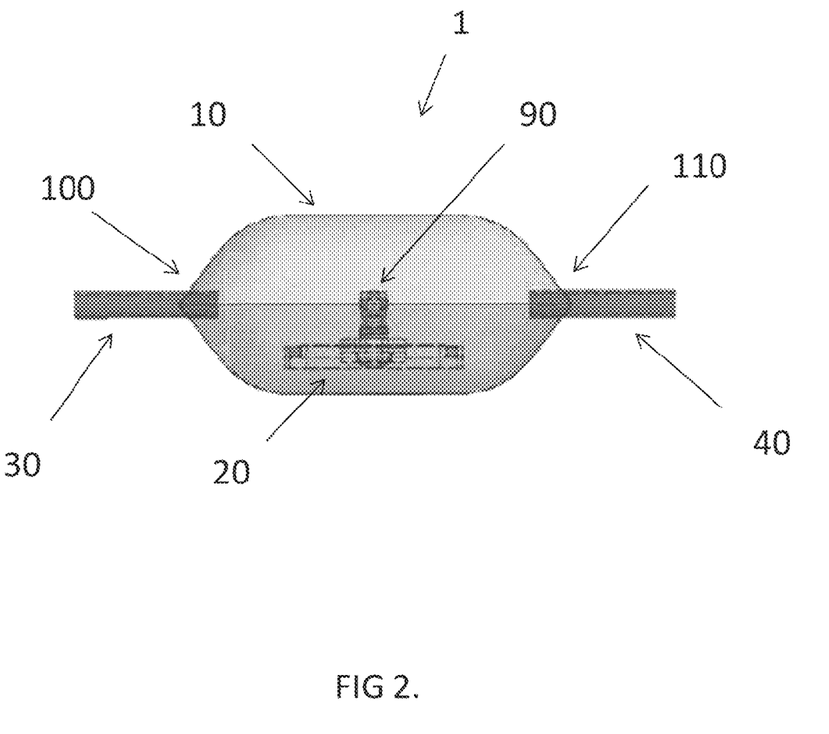
FIG. 2 shows a side-plan view of a cell culture apparatus having double bag assembly.

FIG. 2 shows a side-plan view of double bag assembly. The tubes of ports 30 and 40 enter outer bag 10 at seams 100 and 110 where the FEP sheets are bonded together. Elbow 90 may be angled from 0 to 90 degrees to position inner bag 20 inside outer bag 10. Third port 50 is used for adding and removing cells.

Positioning of inner bag 20 inside the outer bag 10 allows inner bag 20 to be in contact with the media contained within outer bag 10.

In a preferred embodiment inner bag 20 is submerged in the media of outer bag 10 to allow media to permeate in and out of cell culture compartment 60 of inner bag 20.

The tube and elbow 90 of third port 50 each individually, may comprise FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifluoroethylene-vinylidene fluoride copolymer), and TFE/HFP (tetrafuoroethylene-hexafuoropropylene copolymer), or mixtures thereof.

In a preferred embodiment the fluoropolymer tube of third port 50 is FEP (fluorinated ethylene-propylene) and elbow 90 of third port 50 is PFA (perfluoroalkoxy polymer).

Elbow 90 of third port 50 is bonded at one end to the fluoropolymer tube and at the second end to the inner bag so elbow 90 joins the fluoropolymer tube and inner bag 20 in port 50.

The method of bonding may comprise laser welding, corona discharge, radiation, extreme heat or melt lamination, etching, plasma treatment, wetting, adhesives, or combinations thereof.

In a preferred embodiment PFA elbow 90 is laser welded to FEP inner bag 20 and the FEP tube of port 50. Furthermore the FEP tube is laser welded to FEP outer bag 10 where it exits the FEP outer bag 10.

Inner bag volumes may be less than the outer bag volumes and may range from 50 mL to 50 L, 250 mL to 10 L, but preferably 500 mL to 2 L.

Suitable growth media include appropriate media for the choice of cell cultured.

Suitable cells include, for example connective tissue cells, skeletal cells, cardiac cells, epithelial cells, neural cells, endocrine cells, immune cells, lymphocytes, melanocytes, tumor cells, or mixtures thereof.

In one embodiment, in a first paragraph (1), the present invention provides a bag comprising an outer bag and an inner bag, wherein the outer bag comprises a gas permeable film having a first port and a second port attached thereto; and the inner bag comprises a gas permeable film having a third port attached thereto that passes through the outer bag to the inner bag, further provided the gas permeable film of the inner bag has increased pore size.

2. The bag according to paragraph 1, wherein the gas permeable film of the outer bag is FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifluoroethylene-vinylidene fluoride copolymer), and TFE/HFP (tetrafuoroethylene-hexafuoropropylene copolymer), or mixtures thereof.

3. The bag according to paragraph 1, wherein the first and second ports of the outer bag comprise tubes attached to the outer bag.

4. The bag according to paragraph 1, wherein the third port of the inner bag comprises a tube attached to the inner bag.

5. The bag of either paragraph 3 or 4, wherein the tubes are attached to the bags by chemical bonding, adhesive bonding, thermal fusion bonding, solvent bonding, laser welding, surface treatment, or combinations thereof.

6. The bag of either paragraph 3 or 4, wherein the nonbonded ends of the tubes provide a sealable access into the interior of the bags.

7. The bag according to paragraph 1, wherein the gas permeable film of the inner bag is FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or mixtures thereof.

8. The bag according to paragraph 7, wherein the pore size of the fluoropolymer film of the inner bag is between about 1 microns to about 6 microns in diameter.

9. The bag according to paragraph 7, wherein the pore size of the fluoropolymer film of the inner bag is between about 1.5 microns to about 5 microns in diameter.

10. The bag according to paragraph 7, wherein the pore size of the fluoropolymer film of the inner bag is between about 2 microns to about 4 microns in diameter.

11. The bag according to paragraph 7, wherein the pore size of the fluoropolymer film of the inner bag is between about 2.5 microns to about 3.5 microns in diameter.

12. The bag according to paragraph 7, wherein the pore size of the fluoropolymer film of the inner bag is about 3 microns in diameter.

13. The container according to paragraph 7 through 12, wherein the average pore volume is between about 20% to about 55%.

14. The container according to paragraph 7 through 13, wherein the average pore volume is between about 30% to about 50%.

15. The container according to paragraph 7 through 14, wherein the average pore volume is between about 40% to about 45%.

16. The bag according to paragraph 1, wherein the inner bag is secured by a fluoropolymer frame and beading.

17. The bag according to paragraph 10, wherein the fluoropolymer frame and beading are each individually PTFE, FEP, or PFA.

18. A method to cultivate cells in a bag comprising the step of: a) adding cells to the bag, wherein the bag comprises an outer bag and an inner bag, wherein the outer bag comprises an gas permeable film having a first port and a second port attached thereto; and the inner bag comprises a gas permeable film having a third port attached thereto that passes through the outer bag to the inner bag, further provided the fluoropolymer film of the inner bag is porous, wherein the cells are contained in the inner bag.

19. The method according to paragraph 18, wherein the cells comprise connective tissue cells, skeletal cells, cardiac cells, epithelial cells, neural cells, endocrine cells, immune cells, lymphocytes, melanocytes, tumor cells, or mixtures thereof.

20. The method according to paragraph 18, further comprising the step of adding media to the bag, wherein the media is contained within the outer bag and the inner bag.

21. The method according to paragraph 20, further comprising the step of incubating the bag.

22. The method according to paragraph 18, wherein the diameter of the pores is sufficient to retain the cells within the inner bag.

23. The method according to paragraph 20, wherein media can be added through the first port and removed through the second port.

24. The method according to paragraph 19, wherein cells can be introduced or removed through the third port.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A bag comprising;
a gas-permeable outer bag comprising an $O_2$- and $CO_2$-permeable porous film and having a fluid-accessible interior volume, the outer bag having a first port and a second port attached thereto, each of the first and second port providing a fluid connection to the interior volume of the outer bag; and
a gas-permeable, framed inner bag disposed within the outer bag, the inner bag having a fluid-accessible interior volume, the inner bag comprising a sheet of an $O_2$- and $CO_2$-permeable porous film having a third port attached thereto that passes through the interior volume of the outer bag to the inner bag, the framed inner bag being supported by a frame,
wherein
the inner bag is smaller in size in all dimensions than the outer bag, and is connected to the outer bag only through the third port, such that the inner bag is configured to be surrounded in all directions by media disposed in the interior volume of the outer bag,
the inner bag has a pore size that allows for movement of media between the inner bag and the outer bag,
the outer bag has a pore size sufficient to contain media within the outer bag, and
the pore size of the inner bag is larger than the pore size of the outer bag.

2. The bag of claim 1, wherein the $O_2$- and $CO_2$-permeable porous film of the outer bag is a fluoropolymer film selected from FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), and mixtures thereof.

3. The bag of claim 1, wherein the first and second ports of the outer bag comprise tubes attached to the outer bag.

4. The bag of claim 1, wherein the third port of the inner bag comprises a tube attached to the inner bag and passing through the interior volume of the outer bag.

5. The bag of claim 1, wherein the first port of the outer bag comprises a first tube bonded to the outer bag, the second port of the outer bag comprises a second tube bonded to the outer bag, and the third port of the outer bag comprises a third tube bonded to the $O_2$- and $CO_2$-permeable porous film of the inner bag, wherein the tubes are bonded to the bags by chemical bonding, adhesive bonding, thermal fusion bonding, solvent bonding, laser welding, surface treatment, or combinations thereof.

6. The bag of claim 5, wherein the tubes have a non-bonded end, the nonbonded ends of the tubes provide a sealable access into the interior volumes of the bags.

7. The bag of claim 1, wherein the $O_2$- and $CO_2$-permeable porous film of the inner bag is a fluoropolymer film selected from FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), and mixtures thereof.

8. The bag of claim 7, wherein the pore size of the gas permeable porous film of the inner bag is between about 1 microns to about 6 microns in diameter.

9. The bag of claim 7, wherein the pore size of the gas permeable porous film of the inner bag is between about 13 microns to about 5 microns in diameter.

10. The bag of claim 7, wherein the pores have an average pore volume between about 20% to about 55%.

11. The bag of claim 7, wherein the pores have an average pore volume between about 30% to about 50%.

12. The bag of claim 1, wherein the frame is a fluoropolymer frame, and wherein the inner bag comprises a first sheet of a $O_2$- and $CO_2$-permeable porous film and a second sheet of a gas-permeable porous film, with the edges of the first and the second sheet being secured to the fluoropolymer frame by a beading.

13. The bag of claim 12, wherein the fluoropolymer frame and beading are each individually PTFE, FEP, or PFA.

14. The bag of claim 1, wherein the third port is the only port in direct fluid communication with the interior volume of the inner bag without requiring fluid to pass through pores of the inner bag.

15. The bag of claim 1, wherein the inner bag comprises two sheets of gas-permeable porous fluoropolymer that are joined together at their edges to form a sealed cell culture compartment.

16. The bag of claim 1, having a cell culture disposed in the inner bag.

17. The bag of claim 1, wherein the gas permeable porous film of the outer bag is FEP (fluorinated ethylene-propylene).

18. The bag of claim 16, wherein the average pore volume is between about 30% to about 50%.

19. A method to cultivate cells in a bag comprising:
providing a bag according to claim 1; and
adding cells to the bag,
wherein the cells are contained in the inner bag.

20. The method of claim 19, wherein the cells comprise connective tissue cells, skeletal cells, cardiac cells, epithelial cells, neural cells, endocrine cells, immune cells, lymphocytes, melanocytes, tumor cells, or mixtures thereof.

21. The method of claim 19, further comprising the step of adding media to the bag, wherein the media is contained within the outer bag and the inner bag.

22. The method of claim 21, further comprising the step of incubating the bag.

* * * * *